(12) United States Patent
Watts et al.

(10) Patent No.: US 8,491,932 B2
(45) Date of Patent: Jul. 23, 2013

(54) COMPOSITIONS FOR THE ORAL DELIVERY OF CORTICOSTEROIDS

(75) Inventors: Peter Watts, Nottingham (GB); Ann Margaret Dyer, Nottingham (GB)

(73) Assignee: Archimedes Development Limited, Nottingham (GB)

( * ) Notice: Subject to any disclaimer, the term of this patent is extended or adjusted under 35 U.S.C. 154(b) by 0 days.

(21) Appl. No.: 12/992,182

(22) PCT Filed: May 7, 2009

(86) PCT No.: PCT/GB2009/001150
§ 371 (c)(1),
(2), (4) Date: Jan. 21, 2011

(87) PCT Pub. No.: WO2009/138716
PCT Pub. Date: Nov. 19, 2009

(65) Prior Publication Data
US 2011/0104269 A1    May 5, 2011

(30) Foreign Application Priority Data
May 12, 2008  (GB) .................................. 0808537.5

(51) Int. Cl.
*A61K 9/50* (2006.01)
*A61K 9/22* (2006.01)
*A61K 9/52* (2006.01)
*A61P 29/00* (2006.01)
*A61P 13/12* (2006.01)
*A61P 1/00* (2006.01)

(52) U.S. Cl.
USPC ........... 424/468; 424/457; 424/400; 424/490; 514/174

(58) Field of Classification Search
USPC .................. 424/422, 424, 464, 473, 489, 490
See application file for complete search history.

(56) References Cited

U.S. PATENT DOCUMENTS

| | | | |
|---|---|---|---|
| 4,123,403 A | | 10/1978 | Warner et al. |
| 4,502,888 A | | 3/1985 | Leng et al. |
| 5,681,584 A | * | 10/1997 | Savastano et al. ............ 424/473 |
| 5,914,122 A | | 6/1999 | Otterbeck et al. |
| 5,932,249 A | | 8/1999 | Gruber et al. |
| 6,200,602 B1 | | 3/2001 | Watts et al. |
| 6,239,120 B1 | | 5/2001 | Hallgren et al. |
| 6,423,340 B1 | | 7/2002 | Ulmius |
| 6,534,549 B1 | | 3/2003 | Newton et al. |
| 2005/0089571 A1 | | 4/2005 | Beckert et al. |
| 2009/0004281 A1 | * | 1/2009 | Nghiem et al. ............... 424/490 |
| 2011/0189293 A1 | * | 8/2011 | Padval ......................... 424/489 |

FOREIGN PATENT DOCUMENTS

| | | |
|---|---|---|
| EP | 0754452 A2 | 1/1997 |
| EP | 1302200 A1 | 4/2003 |
| EP | 1487421 A2 | 12/2004 |
| EP | 1527772 A1 | 5/2005 |
| WO | 9107172 A1 | 5/1991 |
| WO | 9508323 A1 | 3/1995 |
| WO | 9535100 A1 | 12/1995 |
| WO | 03080032 A2 | 10/2003 |

OTHER PUBLICATIONS

Klokkers-Bethke et al, "Development of a multiple unit drug delivery system for positioned release in the gastrointestinal tract," Journal of Controlled Release, vol. 15, pp. 105-112 (1991).
Streubel et al," pH-independent release of a weakly basic drug from water-insoluble and -soluble matrix tablets," Journal of Controlled Release, vol. 67, pp. 101-110 (2000).
Pharmaceutics, "The Science and Practice of Pharmacy," M. E. Aulton (ed), 2nd Edition, Churchill Livingstone, Edinburgh (2002).
Rudnic et al, "Oral Solid Dosage Forms," Remington: The Science and Practice of Pharmacy, Chapter 45, Lippincott, Williams and Wilkins, Gennaro (ed), Philadelphia (2000).
Int'l Search Report issued Oct. 8, 2009 in Int'l Application No. PCT/GB2009/001150; Written Opinion.
Surelease: Aqueous Ethylcellulose Dispersion, Colorcon, downloaded from webpage: http://www.colocon.com/literature/marketing/mr/Extended%20Release/Surelease/English/prod_info_19030.pdf, Download date: Jul. 18, 2011, Posting date: Dec. 1, 2000, 3 pages.
Office Action issued Jul. 21, 2011 in EP Application No. 09746033.1.
Office Action issued Jan. 27, 2012 in EP Application No. 09746033.1.
Office Action issued Nov. 24, 2011 in CN Application No. 200980127272.5.
Office Action issued Oct. 30, 2012 in CN Application No. 200980127272.5.

\* cited by examiner

*Primary Examiner* — Walter Webb
(74) *Attorney, Agent, or Firm* — Panitch Schwarze Belisario & Nadel LLP

(57) ABSTRACT

An oral drug delivery composition includes a sustained release component which includes a corticosteroid drug and which is contained within a capsule that has been treated so that the sustained release component is predominately released from the capsule in the intestine following oral administration. A drug delivery composition for delivering a corticosteroid drug to the intestine also includes: (a) a sustained release component comprising a corticosteroid drug, an alkali-containing ethylcellulose material and an acid; and (b) a delayed release component which substantially prevents release of the sustained release component until the composition reaches the intestine following oral administration. The compositions of the invention are useful for treating inflammatory diseases of the gastrointestinal tract, such as Crohn's disease and ulcerative colitis, and for treating glomerulonephritis.

15 Claims, No Drawings

COMPOSITIONS FOR THE ORAL DELIVERY OF CORTICOSTEROIDS

CROSS-REFERENCE TO RELATED APPLICATIONS

This application is a Section 371 of International Application No. PCT/GB2009/001150, filed May 7, 2009, which was published in the English language on Nov. 19, 2009, under International Publication No. WO 2009/138716 A1 and the disclosure of which is incorporated herein by reference, in its entirety.

BACKGROUND OF THE INVENTION

The present invention relates to compositions for the treatment of diseases of the gastrointestinal tract. More particularly, the present invention relates to compositions for the oral delivery of corticosteroids.

Oral corticosteroids are used in the treatment of inflammatory diseases of the gastrointestinal tract, such as Crohn's disease and ulcerative colitis where they act principally topically to suppress the inflammatory response. The use of oral corticosteroids for the treatment of glomerulonephritis via local intestinal action has also been described (U.S. Pat. No. 6,239,120).

Corticosteroids can cause undesirable side-effects if there is long-term systemic exposure, such as Cushings syndrome and osteoporosis. Therefore, corticosteroids are currently typically used to treat the acute symptoms of the diseases mentioned above but are not generally used for long-term treatment.

It is desirable to minimise systemic exposure to corticosteroids. One approach is to use rectal dosage forms such as suppositories and enemas which are effective at delivering drug into the distal regions of the colon. Oral formulations which provide targeted drug delivery to the small intestine and colon have also been devised. These typically comprise tablets or pellets which are coated to prevent drug release in the upper regions of the gastrointestinal tract. Coatings described for this purpose include enteric (gastroresistant) materials which are insoluble in stomach acid and dissolve in intestinal fluid. Materials which are biodegraded by the microflora residing in the colon have also been described, such as in U.S. Pat. No. 6,534,549.

The listing or discussion of an apparently prior-published document in this specification should not necessarily be taken as an acknowledgement that the document is part of the state of the art or is common general knowledge.

BRIEF SUMMARY OF THE INVENTION

It is an object of the present invention to provide an oral drug delivery composition which allows a corticosteroid drug to reach an area to be treated, such as an inflamed part of the bowel in sufficient concentration and for a sufficient length of time to provide a local therapeutic effect. For example, in the case of Crohn's disease, this therapeutic effect may be required in the whole bowel or only in the small intestine or in the case of ulcerative colitis it may be required in the caecum, colon and the rectum. In the case of glomerulonephritis, sufficient drug concentration is required in the lower third of the small intestine and the upper quarter of the large intestine so that the drug can exert its effect through the intestinal wall of these parts of the intestine. In other words, it is an object of the invention to provide an oral drug delivery composition for delivering a corticosteroid drug to the intestine or to a particular part or parts of the intestine.

DETAILED DESCRIPTION OF THE INVENTION

The present invention provides compositions for the oral delivery of a corticosteroid drug. The compositions of the invention are typically formulated so that in use, following oral administration, the drug is delivered to the intestine and in the intestine drug release is controlled to provide sustained release of the drug.

The compositions of the invention provide for delayed and controlled/sustained release of the drug. They comprise a delayed release component and a sustained release component. The delayed release component substantially prevents release of the drug in the stomach; rather release is delayed until the composition reaches the intestine after oral delivery. When the composition reaches the intestine the delayed release component dissolves or disintegrates to allow the sustained release component (and therefore the drug) to be released. The sustained release component prevents immediate release of all of the drug. The drug is released over a period of time as it passes through the intestine.

The invention provides an oral drug delivery composition comprising a sustained release component which comprises a corticosteroid drug and which is contained within a capsule that has been treated so that the sustained release component is predominately released from the capsule in the intestine following oral administration.

Any suitable capsule may be used. Preferably the capsule is a hard capsule, for example, a gelatin, hydroxypropyl methylcellulose, pullulan or starch capsule. Starch capsules are preferred.

The present invention also provides an oral drug delivery composition comprising:

(a) a sustained release component comprising a corticosteroid drug, an alkali-containing ethyl cellulose material and an acid; and (b) a delayed release component which substantially prevents release of the sustained release component until the composition reaches the intestine following oral administration.

Any suitable corticosteroid drug may be used in the present invention. Suitable drugs include, but are not limited to, aclometasone, beclomethasone, betamethasone, clobetasol, hydrocortisone, dexamethasone, flunisolide, methylprednisolone, mometasone, prednisolone, triamcinolone, budesonide, fluticasone, ciclesonide and fludrocortisone. A preferred corticosteroid for use in this invention is budesonide, (16α,17-[(1RS)-butylidenebis(oxy)]-11β,21-dihydroxypregna-1,4-diene-3,20-dione).

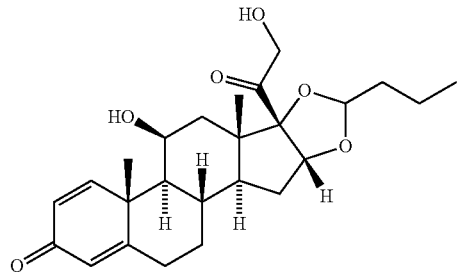

Budesonide

The term "intestine" is used herein to refer to the segment of the alimentary canal which extends from the stomach to the anus and, in humans and other mammals, consists of two parts, the small intestine and the large intestine. In humans, the small intestine comprises the duodenum, jejunum and ileum and the large intestine comprises the caecum and colon.

By the use of phrases such as "delivering a corticosteroid drug to the intestine" or "delivering the sustained release component to the intestine" and "drug is predominately released from the capsule in the intestine" or "the sustained release component is predominately released from the capsule in the intestine" we mean that following oral administration substantially none of the drug is released in the upper regions of the gastrointestinal tract, such as the stomach. For example, no more than 15%, preferably no more than 10% and most preferably no more that 5% of the drug is released from the drug delivery composition before it reaches the intestine. Typically, drug release will start in the small intestine. However, drug release may be substantially delayed until the drug delivery composition reaches the large intestine or may be targeted to start in a particular part of the intestine such as the duodenum, jejunum, ileum, cecum or colon.

The sustained release component controls the rate at which drug is released from the dosage form. More particularly, it controls the rate of drug release once the dosage form has reached the intestine after oral administration.

By the term "sustained release" we mean that not all of the drug is released immediately on the delayed release component dissolving or disintegrating, rather the drug is released over a period of time. The period of time over which the drug is released can be controlled (as will be explained in more detail below) and the desired length of the period over which the drug is release will depend, at least in part, on the condition to be treated.

For humans, it typically takes orally administered substances from 3 to 5 hours to pass through the small intestine and 25 to 50 hours to pass through the large intestine.

It will be appreciated that the release profile (in vitro and in vivo) exhibited by the compositions of the invention will depend on the disease indication to be treated. For example, an appropriate in vivo profile for treatment of Crohn's disease would be minimal (e.g. <5% of dose) release of drug in the stomach with significant release (>5% of dose) beginning in the upper small intestine (duodenum/jejunum) and continuing for from about 6 to about 24 hours. For ulcerative colitis, an appropriate profile would be for significant drug release to begin in the lower small intestine (terminal ileum) or caecum and to continue for from about 6 to 24 hours. For glomerulonephritis, a suitable profile would be for significant drug release to begin in the ileum and to continue for from about 2 to 6 hours or so that drug release occurs predominately in the lower third of the small intestine and the upper quarter of the large intestine.

An appropriate in vitro dissolution test would be to use the European Pharmacopoeia paddle or basket apparatus or United States Pharmacopeia apparatus 1 or 2 and a pH-change methodology such as 2 hours in acid medium followed by a simulated intestinal medium at 37° C. e.g. pH 6.8 phosphate buffer. The table below provides examples of in vitro dissolution profiles which may be appropriate for treating different disease conditions:

| Disease condition | Release in acid (% of dose) | Delay in drug release in simulated intestinal medium | Duration of drug release in simulated intestinal medium |
| --- | --- | --- | --- |
| Crohn's disease | <5% | ≦30 minutes | 6-24 hours |
| Ulcerative colitis | <5% | 90-150 minutes | 6-24 hours |
| Glomerulonephritis | <5% | 30-60 minutes | 2-6 hours |

The sustained release component of the compositions of the invention comprises a corticosteroid drug and a rate-controlling material, such as a rate controlling polymer.

By "rate-controlling material", we mean any material which prevents immediate release of all of the drug as soon as the sustained release component has been released from the delayed release component and provides release of the drug over a period of time.

If the delayed release component is a starch capsule that has been treated so that the sustained release component is predominately released from the capsule in the intestine any suitable rate-controlling material may be used. Examples of suitable rate-controlling materials include, but are not limited to, cellulose derivatives, acrylic polymers and co-polymers, vinyl polymers, methylcellulose, hydroxypropylcellulose, hydroxypropylmethyl-cellulose, ethylcellulose, cellulose acetate, polyvinylpyrrolidone, polyvidone acetate, polyvinyl acetate, polymethacrylates, ethylene-vinyl acetate copolymer and combinations thereof.

A preferred rate-controlling polymer for use in the sustained release element of the compositions of this invention is ethylcellulose. Ethylcellulose is a hydrophobic polymer which forms an excellent barrier to drug diffusion. However, the material is water insoluble and will only form solutions in organic solvents such as chloroform and tetrahydrofuran. Some water-based ethylcellulose coating systems where the polymer is in the form of a latex which fuses to form a continuous layer when dried onto a surface have been developed. Proprietary aqueous ethylcellulose preparations include Surelease® dispersion (Colorcon, West Point, Pa., USA) and Aquacoat® ECD dispersion (FMC Biopolymer, Philadelphia, USA).

Surelease® dispersion is an alkali-containing ethylcellulose material. To produce Surelease® dispersion, ethylcellulose is blended with oleic acid and dibutyl sebacate, then extruded and melted. The molten plasticised ethylcellulose is then directly emulsified in ammoniated water. Ammonium oleate is formed in situ to stabilise and form a dispersion of plasticised ethylcellulose particles (U.S. Pat. Nos. 4,123,403 and 4,502,888). As a result of the inclusion of ammonia, Surelease® dispersion has an alkaline pH.

When the delayed release component is a starch capsule that has been treated so that the sustained release component is predominately released from the capsule in the intestine the rate-controlling material preferably comprises an alkali-containing ethylcellulose material, more preferably an ammonia-containing ethylcellulose, such as Surelease® dispersion.

For other compositions of the invention the rate-controlling material comprises an alkali-containing ethylcellulose material, preferably an ammonia-containing ethylcellulose, such as Surelease® dispersion.

The rate-controlling material may comprise one or more ingredients. For example, a combination of ingredients that control the rate at which the drug is released may be used. By appropriate selection of the or each ingredient of the rate-controlling material the time period over which the drug is released can be controlled.

The rate-controlling material typically comprises an alkali-containing ethylcellulose material. However, it has been found that some alkali-containing ethylcellulose materials, for example ammonia-containing ethylcellulose materials such as Surelease® dispersion, when used alone can provide a significant barrier to corticosteroid release allowing drug to be liberated only slowly. This may be suitable for some applications. However, if there is a need to provide a faster rate of corticosteroid release it is preferable that a water soluble material (ie a material that has a solubility of at least 10 mg/ml in water at 20° C.) is mixed with the alkali-containing ethylcellulose material in order to increase the permeability of the rate-controlling material when placed into an aqueous medium, such as the gastrointestinal tract.

Preferred water soluble materials for inclusion in the rate-controlling material include, but are not limited to, mannitol, dextrose, sucrose, polyethylene glycol, hydroxypropyl methylcellulose, hydroxypropyl cellulose, methylcellulose, triacetin and polyvinyl alcohol.

Although alkali-containing ethylcellulose materials, such as ammonia-containing ethylcellulose, for example Surelease® dispersion, form sustained release components with corticosteroids which have advantageous release profiles, their alkaline nature has been found to cause corticosteroid degradation such that the drug formulation has only a limited shelf life.

Surprisingly, the present inventors have found that the stability of corticosteroid drugs in the presence of an alkali-containing ethylcellulose material can be improved by the incorporation of an acid into the sustained release component of the compositions of the invention.

The acid used is preferably a weak acid. By the term "weak acid" we mean acids which have a pKa of less than about 6.5. Suitable acids include organic acids. Examples of suitable acids include citric acid, glutamic acid, lactic acid, tartaric acid, fumaric acid, malic acid and monobasic sodium phosphate. Especially preferred acids are citric acid, tartaric acid, fumaric acid, malic acid and monobasic sodium phosphate. The most preferred acid is citric acid.

The sustained release component of the compositions of the present invention typically comprises a drug-containing core coated with one or more coating layers. However, other structures are possible. For example, two or more of the drug, the acid and the alkali-containing ethylcellulose material may be contained within a matrix together with one or more suitable inert matrix materials. Such matrixes may, for example, be in the form of microspheres, tablets or beads.

The core typically comprises: a) drug alone as individual or agglomerated crystalline or amorphous particles; b) particles containing a substantially uniform dispersion of drug in an inert matrix (ie the drug is distributed substantially evenly throughout the matrix); or c) inert particles to which a layer of drug has been applied. Cores of types b) and c) are preferred and type c) is especially preferred.

If drug alone is the core then it is preferable that the particles are of substantially uniform size and shape as this can result in more even coating of the core particles. By substantially uniform size, we mean that at least about 90% of the particles have a diameter of from about 0.2 to about 2 mm. Methods for producing drug particles of a substantially uniform size are well known in the art and any suitable method can be used to produce drug particles for use in the invention. Suitable techniques include milling and sieving, spray drying and supercritical fluid technologies.

Methods suitable for producing particles comprising a substantially uniform dispersion of drug in an inert matrix include, but are not limited to, granulation, extrusion-spheronisation, microencapsulation and tabletting.

The preparation of tablet and granule formulations is well known to those skilled in the art. Further details can be found in standard texts, such as Remington, The Science and Practice of Pharmacy (Chapter 45, Lippincott Williams & Wilkins (Ed.), Philadelphia, 2000) and Pharmaceutics, The science of dosage form design (M. E. Aulton (Ed), Churchill Livingstone, Edinburgh, 2002).

Granules may be produced by techniques well known to those skilled in the art such as wet granulation, dry granulation (slugging), fluid bed granulation and spray congealing. In addition to the drug substance, other ingredients incorporated into the granules (to provide an inert matrix) may include diluents such as calcium phosphate, lactose, dextrose, mannitol and microcrystalline cellulose, binders such as povidone (polyvinylpyrrolidone), methylcellulose, polyethylene glycol, gelatin and acacia, disintegrants such as starch, croscarmellose and crospovidone, glidants such as colloidal silica, and lubricants such as magnesium stearate and hydrogenated vegetable oil.

Tablets may be prepared by compressing a blend of individual ingredients or by compressing granules or a blend of granules comprising some of the ingredients. Typical inert ingredients used in tablets include, but are not limited to, diluents such as lactose, microcrystalline cellulose, dextrose, dextrin, starches and dibasic calcium phosphate; binders such as povidone, pregelatinised starch and hydroxypropyl methylcellulose; glidants such as talc and silicon dioxide; lubricants such as hydrogenated vegetable oil and stearic acid and its salts.

Extrusion-spheronisation is a well known process that can be used to form uncoated spherical particles. This process is described in, for example, Pharmaceutics, The science of dosage form design, M. E. Aulton (Ed), 2nd Edition, Churchill Livingstone, Edinburgh, 2002, pages 374-376.

In extrusion-spheronisation, a heavy granule or wet mass is made by mixing drug and suitable excipients with an appropriate quantity of water to produce a granulate. The granulate is then passed through an extruder to produce an extrudate. The extrudate is transferred to a spheroniser. The spheroniser typically comprises a horizontally spinning metal disc having a scored surface, which is typically cross-hatched. When applied to this spinning surface, the extrudate is broken up and transformed into essentially spherical particles, which are then dried to remove water.

Suitable excipients include, but are not limited to, spheronisation enhancers, which impart the binding properties necessary for pellet strength and integrity, and confer the plasticity necessary for extrudate and sphere formation, such as celluloses, for example microcrystalline cellulose; diluents, such as maize starch, corn starch, potato starch, rice starch, tapioca starch, wheat starch; lactose and other sugars such as compressible sugar and dextrates; inorganic salts, such as dibasic calcium phosphate, tribasic calcium phopshate; and polyols, such as mannitol, sorbitol, and xylitol; glidants, such as talc, magnesium, calcium and zinc stearates, stearic acid, colloidal silicon dioxide; disintegrants, such as croscarmellose sodium, starch, sodium starch glycolate, sodium carboxymethylcellulose; other pharmaceutical excipients, including polysaccharides, such as chitosan and chitosan derivatives and chitin derivatives and pectin; xanthan, acacia, tragacanth, locust bean and guar gums; stearates such as, calcium and zinc stearates, and sodium stearyl fumarate; and hydrogenated vegetable oil; and release modifying excipients, such as ethylcellulose, methylcellulose, hydroxypropyl methylcellulose, hydroxypropyl cellulose.

Methods for preparation of microspheres are well known to those skilled in the art and include, but are not limited to, spray drying, interfacial polymerisation, coacervation/phase separation and solvent evaporation. In addition to the corticosteroid drug, microspheres may include ingredients such as starches, dextrans, gelatin, albumin, collagen, hyaluronic acid, chitosan, lactose, sucrose, dextrose, mannitol and celluloses such as methylcellulose.

If the substrate is prepared by applying drug to an inert particle this is preferably achieved by spraying drug onto the inert core. Methods for doing this are well known in the art. The inert core may produced by granulation, extrusion-spheronisation, microencapsulation or tableting, as described above but without the inclusion of drug.

However, the inert core is preferably a commercially-available sugar sphere (often termed non-pareil). Sugar spheres predominantly comprise sucrose with smaller amounts of other materials added, such as starch. Suppliers of sugar spheres include Paulaur Corporation (USA), Chr. Hansen (Denmark), NP Pharm (France), Emilio Castelli (Italy) and JRS Pharma (Germany). Sugar spheres are available in a wide variety of diameters, typically in the range of from about 0.2 to about 5 mm.

The following is a non-limiting example of a method which can be used to apply drug to inert cores. The inert cores may be placed in a coating pan or chamber where they are set in continuous motion and exposed to a current of warm air. The drug and optionally a binder is dissolved or suspended in a volatile liquid vehicle to provide a coating liquid. The coating liquid is applied onto the inert cores, preferably as a fine mist. The liquid vehicle evaporates in the current of warm air to leave a deposit of solid material on the surface of the inert particle. The liquid vehicle is preferably water although non-aqueous solvents such as ethanol, isopropanol and ethyl acetate may also be used.

Suitable binders include, but are not limited to povidone, hydroxypropyl cellulose, hydroxyethyl cellulose, hydroxypropyl methylcellulose and polyvinyl alcohol. Preferred binders include hydroxypropyl cellulose, hydroxyethyl cellulose and hydroxypropyl methylcellulose. Preferably a binder is used.

The coating liquid may optionally contain other ingredients such as a plasticiser (e.g. polyethylene glycol, triacetin or triethyl citrate), an anti-tack agent (e.g. talc or magnesium stearate) or a colouring agent. Preferably the coating liquid contains a binder and one or more of these optional ingredients.

The acid may be incorporated into the drug-containing layer or it may be included in a separate barrier layer between the drug layer and the layer comprising an alkali-containing ethylcellulose material or it may be included in the layer comprising an alkali-containing ethylcellulose material.

If the acid is incorporated into the drug layer the methods described above may be used. For example, an acid may be included in the drug containing coating liquid described above.

Preferably, the acid is provided as a coating layer on the drug-containing core. The acid-containing coating layer comprises the acid and optionally a carrier polymer which will form a flexible adherent film on a surface to which it is applied and/or other optional ingredients such as, but not limited to, plasticisers, anti-tack agents or colours, as described earlier.

Preferred carrier polymers include polyethylene glycol, hydroxypropyl methylcellulose, hydroxypropyl cellulose, methylcellulose and polyvinyl alcohol.

The sustained release component is preferably a multitude of drug-containing units such as coated drug particles, coated pellets, coated granules or coated tablets. The diameter of each of these units is preferably from about 0.025 to about 5 mm, more preferably from about 0.05 to about 4 mm and most preferably from about 0.1 to about 3 mm, for example from about 0.2 to about 1.4 mm.

The corticosteroid content of the sustained release component as a percentage by weight of the sustained release component is preferably from about 0.25 to about 70%, more preferably from about 0.5 to about 60% and most preferably from about 1 to about 50%. When the corticosteroid is budesonide, the drug is preferably present in an amount of from about 0.25 to about 10% by weight of the sustained release component, more preferably from about 0.5 to about 7.5% and most preferably from about 1 to about 5%.

The acid content of the sustained release component as a percentage by weight of the sustained release component is from about 0.01 to about 70%, preferably from about 0.25 to 70%, more preferably from about 0.5 to about 60%, and more preferably from about 0.01 to about 3%, more preferably from about 0.02 to about 2% and most preferably from about 0.05 to about 1%.

The rate-controlling material is preferably present in the sustained release component in an amount of from about 0.25 to about 15% by weight of the sustained release component, more preferably from about 0.5 to about 12% by weight and most preferably from about 1 to about 10% by weight.

Where the rate-controlling material comprises an alkali-containing ethylcellulose material, for example an ammonia-containing ethylcellulose such as Surelease® dispersion, the amount of water soluble material in the rate controlling material is preferably from about 2 to about 50% by weight of the alkali-containing ethylcellulose (as solids), more preferably from about 5 to about 40% by weight and most preferably from about 10 to about 30% by weight.

The preferred means of producing the sustained release element of the compositions of this invention is by layering polymers onto a substrate.

A preferred means to prepare the sustained release element of this invention is to take sugar spheres having an average diameter of from about 0.2 to about 1.4 mm, for example from about 1.0 to about 1.2 mm and apply a layer comprising a corticosteroid drug by spray coating (as described above). The coating liquid is preferably water in which a corticosteroid is dissolved or suspended and which also comprises a dissolved binding agent and optionally a plasticiser. The binding agent is preferably hydroxypropyl methylcellulose. The plasticizer, if used, may be polyethylene glycol, triacetin or triethyl citrate. Onto the drug layer is applied an acid-containing barrier layer using a solution of organic acid, such as citric acid, and binder, such as hydroxypropyl methylcellulose and optionally a plasticiser, in a volatile solvent such as water. Any suitable method such as spray coating can be used to apply the barrier layer. A rate-controlling layer is applied onto the barrier layer using an aqueous ethylcellulose preparation comprising an alkali-containing ethylcellulose material, for example Surelease® dispersion, and optionally a water-soluble component.

The sustained release component is preferably contained within a hard capsule. For example, a gelatin, hydroxypropyl methylcellulose, pullulan or starch capsule. Starch capsules are preferred.

To provide delayed release of the sustained release component either the sustained release component or the capsule in which it is contained is treated, for example coated, with a material that substantially prevents release of the sustained release component until the composition reaches the intestine, for example the lower small intestine. It is preferred to treat, for example coat, the capsule which contains the sustained release component with a material that substantially prevents release of the sustained release component until the composition reaches the intestine.

The preferred delayed release materials are polymers that have gastroresistant properties. Gastroresistant materials or polymers may be insoluble in the low pH of the stomach but dissolve in the higher pH environment of the intestine, for example in the small intestine, for example they may dissolve at a pH of about 5 or above, or they may be redox-sensitive or they may be degraded by enzymes or bacteria present in the intestine, for example those present in the colon.

Examples of polymers with gastroresistant properties which may be used in the invention include, but are not limited to, cellulose acetate trimellitate (CAT), hydroxypropyl methylcellulose phthalate (HPMCP), polyvinyl acetate phthalate (PVAP), cellulose acetate phthalate (CAP), shellac, azopolymers, disulphide polymers, methylmethacrylate and copolymers of methacrylic acid and methylmethacrylate. The latter polymers have monographs in the United States Pharmacopeia, where they are referred to as "methacrylic acid copolymers", and in the European Pharmacopoeia, where they are referred to as "methacrylic acid-methyl methacrylate copolymer (1:1)" and "methacrylic acid-methyl methacrylate copolymer (1:2)". The different ratios of free carboxyl groups to the ester provides different solubility characteristics: methacrylic acid-methyl methacrylate copolymer (1:1) dissolves when the pH exceeds 6 and methacrylic acid-methyl methacrylate copolymer (1:2) dissolves when the pH exceeds 7. Commercial sources of methacrylic acid-methyl methacrylate copolymer (1:1) and methacrylic acid-methyl methacrylate copolymer (1:2) are Eudragit® L100 copolymer and Eudragit® S100 copolymer respectively (Degussa, Germany).

For simplicity, the preferred delayed release materials (eg coating compositions) are described using the Eudragit® copolymer names although polymers with the same chemical structure from other suppliers would be equally suitable.

Especially preferred coating compositions are based on Eudragit® L100 copolymer and Eudragit® S100 copolymer in the range of about 100 parts L100: about 0 parts S100, to about 20 parts L100: about 80 parts S100. The most preferable range is about 70 parts L100:to about 30 parts S100, to about 80 parts L100: about 20 parts S100. The coating may optionally comprise ingredients such as anti-tack agents (e.g. talc, magnesium stearate), plasticisers (e.g. phthalate esters, dibutyl sebacate) and colours.

Expressed as mg of coating per $cm^2$ of surface area, the amount of delayed release coating on a capsule or the sustained release component is preferably from about 1 to about 30 mg/$cm^2$, more preferably from about 2 to about 25 mg/$cm^2$ and most preferably from about 3 to about 20 mg/$cm^2$. Thus, a capsule with a surface area of about 5 $cm^2$ most preferably contains from about 15 to about 100 mg of coating.

As examples of particular coatings that are suitable for use in the present invention, a coating layer of from about 3 to 6 mg/$cm^2$ may be suitable for a dosage form intended for use in the treatment of Crohn's disease, a coating layer of from about 6 to 10 mg/$cm^2$ may be suitable for a dosage form intended for use in the treatment of glomerulonephritis and a coating layer of from about 10-20 mg/$cm^2$ may be suitable for a dosage form intended for use in the treatment of ulcerative colitis. It will be appreciated that the thickness of the coating layer will depend on the nature of the coating material as well as the condition to be treated. The coating thicknesses given above are particularly (although not exclusively) suitable when the coating is a 75 parts:25 parts Eudragit® L100:S100 copolymer system.

The person of ordinary skill in the art will be able to readily determine an appropriate coating thickness for a given coating material using the in vitro dissolution test described above.

In a particularly preferred aspect, a capsule, such as a starch capsule as described in International Patent Application Publication No. WO95/35100, is used in the drug delivery compositions of the invention.

Preferred oral drug delivery compositions of the invention comprise a sustained release component which comprise a core comprising budesonide, an acid-containing barrier layer, which preferably comprises citric acid and a layer comprising a sustained release component comprising an ammonia-containing ethylcellulose such as Surelease® dispersion and is contained within a starch capsule, which is coated with a delayed release material which substantially prevents release of the sustained release component until the composition reaches the intestine and which preferably comprises Eudragit® L100 copolymer and/or Eudragit® S100 copolymer.

The oral drug delivery compositions of the invention may additionally comprise some corticosteroid drug formulated for immediate release. By this we mean that a proportion of the corticosteroid drug, for example up to about 50%, is in a form such that it is released immediately on the delayed release component dissolving or disintegrating.

The present invention also provides the use of an alkali-containing ethylcellulose material and an acid in the manufacture of a medicament for the sustained release of a corticosteroid drug.

The compositions of the invention can be used for the treatment of inflammatory diseases of the gastrointestinal tract, such as Crohn's disease or ulcerative colitis. The compositions of the invention can also be used for the treatment of glomerulonephritis.

The present invention provides the use of:

a sustained release component comprising a corticosteroid drug, an alkali-containing ethyl cellulose material and an acid; and a delayed release component which substantially prevents release of the sustained release component until the composition reaches the intestine following oral administration, or a composition of the invention in the manufacture of a medicament for the treatment of inflammatory diseases of the gastrointestinal tract, such as Crohn's disease or ulcerative colitis, or glomerulonephritis.

The present invention provides a method of treating inflammatory diseases of the gastrointestinal tract, such as Crohn's disease or ulcerative colitis, which method comprises administering a composition of the invention to a patient.

The present invention provides a method of treating glomerulonephritis, which method comprises administering a composition of the invention to a patient.

The invention is illustrated by the following non-limiting Examples.

EXAMPLE 1

Preparation of Sustained Release Budesonide Beads (i) Coating Solution Containing Drug 258 g of a hydroxypropyl methylcellulose/polyethylene glycol blend (Opadry® coating material, Colorcon, Dartford, UK) was dissolved by vigorously stirring into 2970 g of water. 72 g of micronised budesonide (Sicor, Italy) was then vigorously stirred into the Opadry® coating material solution to form a uniform suspension. The suspension was made up to a weight of 3300 g using water.

(ii) Acidified Sealant Layer 144 g of Opadry® coating material (as described above) and 6 g of citric acid (Thornton and Ross) were dissolved in 1350 g of water. The solution was made up to 1500 g with water.

(iii) Applying Drug and Sealant Layers

The coating chamber of an Aeromatic-Fielder™ MP-1 fluidised bed coater was charged with 4000 g of sugar spheres (16-18 mesh size, Paulaur, USA) and the following settings used:

Fluidisation air volume=80 m³/h
Inlet temp=70° C.
Atomisation pressure=29 psi (2 bar)

2906 g of budesonide/Opadry® coating material coating dispersion (obtained in step (i)) was applied at an approximate rate of 15 g/min. After the coating had been applied, fluidisation was continued for 15 minutes at 60° C. to dry the beads. The inlet temperature was then reduced to 50° C. and 1200 g of sealant layer solution (obtained in step (ii) was applied at an approximate rate of 10 g/min. Finally, the beads were dried at 50° C. for 15 minutes followed by 15 minutes at 30° C.

The dried beads were passed through a 1.4 mm sieve and over a 0.5 mm sieve to remove any oversize and undersize particles. The yield of product was 4.24 kg.

(iv) Controlled Release Layer 900 g of Surelease® dispersion (ethylcellulose aqueous dispersion, 25% by weight solids) was transferred to a beaker. 45 g of Opadry® coating material (hydroxypropyl methylcellulose/polyethylene glycol blend) was dissolved in 555 g of water and the resulting solution gently mixed into the Surelease® dispersion.

4 kg of the coated beads (obtained in step (iii)) were transferred into the coating chamber of the MP-1 coater which was set up with the following parameters:

Fluidisation air volume=80 m³/h
Inlet temp=70° C.
Atomisation pressure=29 psi (2 bar)

778 g of coating dispersion was applied to the beads at an approximate rate of 9 g/min. The coated beads were dried while being fluidised for 15 minutes at 60° C. followed by 15 minutes at 30° C.

EXAMPLE 2

Preparation of Coated Capsules Containing Budesonide Beads (a) Capsule Filling

The budesonide beads (obtained in Example 1) were filled into size 0 starch capsules (Capsugel, Greenwood, S.C. USA): Each capsule body was filled with 282 mg of beads, equivalent to 4 mg of budesonide and a lid was sealed onto each body using a water/isopropanol mixture.

(b) Capsule Coating 47.5 g Eudragit® L100 copolymer and 15.8 g Eudragit® S100 copolymer (Degussa, Darmstadt, Germany) were dissolved in a mixture comprising 714 g isopropanol and 24.3 g water. 12.2 g of dibutyl sebacate (plasticiser) and 15.8 g talc (anti-tack agent) were mixed into the coating solution.

2400 filled capsules were transferred to the pan of a Hi-Coater™ device (Vector Corporation, USA) and rotated at a speed of 18 rpm. The inlet temperature was set at 40° C. and the air flow at 1.16 m³/min (41 ft³/min) and the capsules warmed for 10 minutes. Coating dispersion was then applied using a pressure of 18 psi and an application rate of approximately 20 g/min.

After all of the dispersion had been applied capsules were dried in the coating pan for 20 minutes at 40° C. and then transferred to trays and dried at room temperature for 18 hours.

The capsules are suitable for use in the treatment of glomerulonephritis.

EXAMPLE 3

Long-term Stability of Coated Capsules Containing Budesonide Beads

The table below lists the budesonide and impurities content of the capsules prepared in Example 2 and stored in HDPE bottles fitted with child resistant polypropylene caps for 30 months at 25° C./60% RH. Both parameters remained well within specification at 30 months indicating excellent stability of budesonide within the bead formulation.

| | | Time (months) | | | | |
|---|---|---|---|---|---|---|
| Parameter | Specification | 0 | 6 | 12 | 18 | 30 |
| Budesonide content (mg per capsule) | 3.6-4.4 mg per capsule | 3.82 | 3.70 | 3.88 | 3.89 | 3.73 |
| Total impurities (% relative to budesonide) | Not more than 2% | 0.0 | 0.2 | 0.4 | 0.3 | 0.5 |

EXAMPLE 4

Effect of Including an Organic Acid Layer on Stability of Coated Budesonide Beads Two batches of coated sugar spheres were produced following the processes described in Example 1.

Batch 1

An aqueous solution was prepared containing 22% w/w budesonide suspended in Opadry® coating material (78% w/w). 1500 g of sugar spheres were coated with this dispersion to a weight gain of 6.4%. The final coated spheres contained 1.3% w/w budesonide.

The drug-coated spheres were coated with 500 g of 10% w/w aqueous Opadry® coating material solution.

A coating dispersion was prepared containing 480 g Surelease® dispersion (=120 g solids), 24 g Opadry® coating material and 396 g water. This coating dispersion was applied to 1500 g of coated spheres.

Batch 2

An aqueous solution was prepared containing 22% w/w budesonide suspended in Opadry® coating material (78% w/w). 1500 g of sugar spheres were coated with this solution to a weight gain of 6%. The final coated spheres contained 1.3% w/w budesonide.

The drug-coated spheres were coated with 500 g of an aqueous solution containing 9.6% w/w Opadry® coating material and 0.4% w/w citric acid.

A coating dispersion was prepared containing 480 g Surelease® dispersion (=120 g solids), 24 g Opadry® coating material and 396 g water. This coating dispersion was applied to 1500 g of coated spheres.

A sample of the beads from each of Batches 1 and 2 was stored in a glass vial in an incubator at 60° C. for 7 days to accelerate any drug degradation. Samples were then analysed by High Performance Liquid Chromatography for budesonide degradation products: A number of peaks were associated with budesonide degradation and the sum of the peak areas was calculated. The summed peak area was divided by the peak area of budesonide and multiplied by 100 to determine the % of degradation products present (relative to budesonide).

The bead formulation prepared without the citric acid layer contained 1% budesonide degradation products whereas the beads with the layer of citric acid contained only 0.3% budesonide degradation products. This demonstrated that the incorporation of an acidified layer between drug and Surelease® dispersion reduces degradation of drug.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. An oral drug delivery composition for providing sustained release of budesonide to a subject's intestine comprising:
    (a) a sustained release component comprising a core comprising budesonide, wherein the core is coated with a layer comprising an acid, and the acid-containing layer is coated with a layer comprising an alkali-containing ethylcellulose; and
    (b) a delayed release component which substantially prevents release of the sustained release component until the composition reaches the intestine following oral administration to the subject.

2. A composition according to claim 1, wherein the alkali-containing ethylcellulose material is an ammonia-containing ethylcellulose material.

3. A composition according to claim 1, wherein the layer comprising the alkali-containing ethylcellulose further comprises a water soluble material selected from mannitol, dextrose, sucrose, polyethylene glycol, hydroxypropyl methylcellulose, hydroxypropyl cellulose, methylcellulose, triacetin and polyvinyl alcohol.

4. A composition according to claim 1, wherein the acid is an organic acid.

5. A composition according to claim 1, wherein the sustained release component comprises coated drug particles, coated pellets, coated granules or coated tablets.

6. A composition according to claim 1, wherein the sustained release component is contained within a capsule.

7. A composition according to claim 6, wherein the capsule is a starch capsule.

8. A composition according to claim 6, wherein the capsule is coated with the delayed release component (b).

9. A method for treating an inflammatory disease of a subject's gastrointestinal tract, the method comprising orally administering to the subject the composition of claim 1.

10. A method for treating Crohn's disease of a subject, the method comprising orally administering to the subject the composition of claim 1.

11. A method for treating ulcerative colitis of a subject, the method comprising orally administering to the subject the composition of claim 1.

12. A method for treating glomerulonephritis of a subject, the method comprising orally administering to the subject the composition of claim 1.

13. A method for sustained release of a corticosteroid drug administered to a subject, the method comprising orally administering to the subject a composition according to claim 1.

14. A composition according to claim 1 in which the alkali-containing ethylcellulose is present in the sustained release component in an amount of from about 1% to about 10% by weight of the sustained release component.

15. A method according to claim 12 for the treatment of glomerulonephritis, which provides a duration of drug release of from about 2 to about 6 hours.

* * * * *